United States Patent [19]
Espitalie et al.

[11] 3,953,171
[45] Apr. 27, 1976

[54] METHOD AND APPARATUS FOR RAPIDLY EVALUATING THE HYDROCARBON PRODUCTION CAPACITY OF SEDIMENTS, USING SMALL SAMPLES THEREOF

[75] Inventors: Jean Espitalie, Le Vesinet; Bernard Durand, Rueil-Malmaison, both of France

[73] Assignee: Institut Francais du Petrole, des Carburants et Lubrifiants, France

[22] Filed: Apr. 22, 1974

[21] Appl. No.: 463,185

[30] Foreign Application Priority Data
Apr. 27, 1973 France .............................. 73.15348

[52] U.S. Cl. ....................... 23/230 EP; 23/230 PC; 23/253 PC
[51] Int. Cl.² .................. G01N 31/12; G01N 33/24
[58] Field of Search.... 23/230 EP, 230 PC, 253 PC, 23/254 R

[56] References Cited
UNITED STATES PATENTS

| | | | |
|---|---|---|---|
| 2,269,569 | 1/1942 | Williams | 23/230 EP X |
| 2,287,101 | 6/1942 | Horvitz | 23/232 R |
| 2,330,716 | 9/1943 | Horvitz | 23/230 EP |
| 2,334,269 | 11/1943 | Kiss | 23/230 EP |
| 2,336,176 | 12/1943 | Horvitz | 23/230 EP |
| 2,376,145 | 5/1945 | Horvitz | 23/254 R |
| 2,406,611 | 8/1946 | Kennedy | 23/230 EP |
| 2,600,158 | 6/1952 | Clothier | 23/230 EP |
| 3,303,002 | 2/1967 | McAuliffe | 23/230 EP |
| 3,446,597 | 5/1969 | Bray et al. | 23/230 EP |
| 3,518,059 | 6/1970 | Levy | 23/232 R |

*Primary Examiner*—Robert M. Reese
*Attorney, Agent, or Firm*—Craig & Antonelli

[57] ABSTRACT

The method comprises the steps of heating a sample of sediments, determining a group of two parameters $S_1$ and $S_2$ which represent, respectively, the amounts of at least one hydrocarbon compound and of at least one oxygen-containing compound formed by heating the organic material contained in the sediment, and evaluating from the determination of this group of parameters the capacity of the sediments to constitute a good mother rock (i.e. source) for hydrocarbons.

31 Claims, 5 Drawing Figures

FIG.1A

METHOD AND APPARATUS FOR RAPIDLY EVALUATING THE HYDROCARBON PRODUCTION CAPACITY OF SEDIMENTS, USING SMALL SAMPLES THEREOF

The present invention relates to a method and an apparatus for rapidly evaluating the hydrocarbon production capacity of geological sediments, using small samples thereof.

The samples may be taken at the ground surface or in a well bore (using, for example, cores, cuttings, etc. . . .).

Furthermore the invention may provide indications as to the composition of the organic material contained in the sediments.

The methods heretofore used to obtain such informations require preliminary physico-chemical treatments of the sediments, in order, for example, to separate the organic material thereof from the mineral matrix, and entails various analyses which, on the whole, may last several days.

Moreover, for practising these prior art methods, it is necessary to take substantial amounts of samples (about 100 grams) of the sedimentary rock to be analyzed.

The invention provides a method and an apparatus giving within a few tens of minutes (e.g. 20 to 30 minutes) the desired informations, from ground samples not exceeding a few milligrams and only requiring a preliminary grinding operation.

The invention will be properly understood and other advantages thereof will become apparent from the following description of a non-limitative embodiment, illustrated by the accompanying drawings wherein:

FIG. 1 diagrammatically illustrates an apparatus for carrying out the invention.

FIG. 1 A illustrates a modification of this apparatus.

Figure 1:
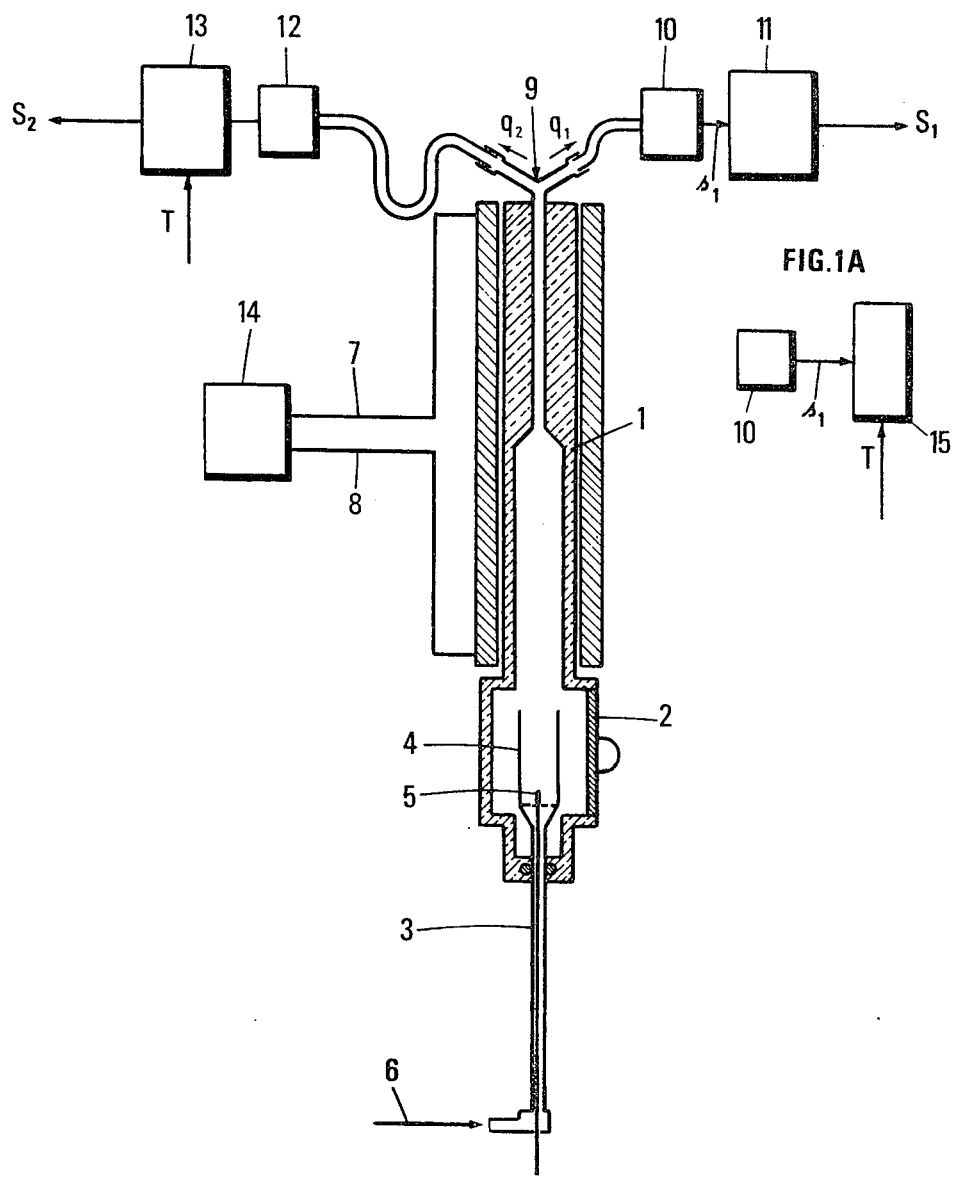

The apparatus according to the invention, as illustrated by FIG. 1, comprises a heating tube 1 or a tube which can be heated, in the extension of an inlet tight chamber 2, wherein a piston head 3 can receive the sample to be studied, in a cup 4.

The piston 3 houses a thermocouple 5 and permits to introduce a scavenging gas into the device at 6, this gas being for example an inert gas (argon, helium, nitrogen. etc. . . ), or hydrogen.

In order to effect the analysis, the piston 3 can be introduced upwardly into the heated part of tube 1 by vertical motion either manually or through the intermediary of a suitable electric, hydraulic or pneumatic device.

For a rapid cooling of tube 1 after each analysis, the tube and the heating means associated thereto must have a low thermal inertia.

The tube 1 may be heated through a low voltage direct electric current (using an electrically conductive tube 1) or through an external heating system of low thermal inertia.

A heating device comprising a conventional furnace may optionally be used, but does not provide for a fast cooling in the present case.

The electric current supply of the heating system is achieved through conductors 7 and 8. Heating is controlled through a programming device 14 which may be of a conventional type, to which is connected a thermal detector means (not shown) continuous by measuring the temperature in the tube 1.

By using the apparatus according to the invention, as illustrated by FIG. 1, we can determine, through pyrolysis of the organic material contained in the sediments two parameters which are respectively proportional to the quantities of hydrocarbon and oxygen compounds (such as carbon dioxide and water) contained in these sediments and produced by this pyrolysis.

As hereinabove indicated, this pyrolysis can be effected under a flow of inert gases, such as argon, helium, nitrogen, etc. . . , or under a flow of hydrogen.

This pyrolysis may be performed on any sample of sediments which has not been subjected to a preliminary treatment, but also on sediments which have undergone certain treatments, such as an extraction therefrom of hydrocarbons, resins and asphaltenes by means of an organic solvent, such as chloroform, a decarbonation of the mineral matrix through an acid (for example hydrochloric acid).

The invention is also suitable for characterizing some materials, such as ground samples, recent sediments, nonsedimentary rocks, coals, as well as for studying any type of organic material of any origin.

The analysis can be performed during a programmed heating, the progressive temperature rise being for example from 1°C/minute to 50°C/minute, preferably from 5°C/minute to 20°C/minute. The analysis may then comprise the following steps:

determining a parameter $S_1$ substantially proportional to the quantity of at least one hydrocarbon compound (other than the hydrocarbons already present in the sediments) produced by heating to a temperature of 600°C, determining a parameter $S_2$ substantially proportional to the quantity of at least one oxygen-containing compound (mainly $CO_2$ and/or $H_2O$) issued from the organic material of the sample and produced within the temperature range of from about 150°C to about 400°–450°C (when the products released from the sample at 150°C are taken into account for the determination of $S_2$, the measurement may become inaccurate due to the carbon dioxide which is simply absorbed by the sediments, or which results from the decomposition of the bicarbonates, and also mainly to the presence of hydration water in some minerals, such as gypsum, while above a temperature of about 450°C the carbonates of the mineral matrix are decomposed, particularly the iron carbonates, and a dehydroxylation of the clayish mineral occurs which would lead to erroneous measurements).

The upper part of tube 1, whose diameter is narrowed so as to give a shorter response time of the analysing devices, is provided at its top with a device 9 dividing the gas flow into two portions. One of these portions, whose flow rate is $q_1$ (the ratio of $q_1$ to the overall flow rate $q_1 + q_2$ at the outlet of tube 1 has a constant value for the apparatus) is directed toward a device 10 for detecting the content is this fraction of one or more hydrocarbon compounds, this content being expressed by the outlet signal $S_1$ of the apparatus 10.

This detection device will, for example, include a detector of the ionizing flame type, which is conventionally used on gas chromatography analyses.

The inlet part of this device will, for example, be kept at a temperature of about 550° C, so as to prevent any condensation of the hydrocarbon compounds in the gas flow upstream of the device 10.

This device 10 is connected to an integrating device 11 delivering a signal $S_1$ which is representative of the quantity of one or several hydrocarbon compounds produced by the sediments up to a temperature of about 600°C.

The other fraction of the gaseous effluent of tube 1, whose flow rate is $q_2$, is directed toward a device 12a for trapping the oxygen-containing compounds. This last device may be formed by a conventional trap with liquid nitrogen or by a solid adsorbent trap (molecular sieve). Through a device for reheating this trap 12a (not shown) these oxygencontaining compounds can be directed toward a device 12 for measuring the quantity of at least one oxygen-containing compound ($CO_2$, $H_2O$) produced by the organic material.

This device 12 may, for example, comprise a catharometer, which is also a conventional detection device for gas chromatography analyses, or any other device for determining the $CO_2$ content, based, for example, on the catalytic conversion of $CO_2$ into methane.

It is also possible to have a device for continuously detecting these oxygen compounds, without the above indicated trapping device.

The device 12 is connected to an integrating device 13 delivering a signal $S_2$ representative of the quantity of one or more oxygen-containing compounds produced by the organic material of the sediments by heating the tube 1 at a temperature from about 150°C to about 450°C.

We have discovered that the organic material contained in the sediments, which can be characterized, for each sample, by the knowledge of the group of the two values $S_1$ and $S_2$ follows during its progressive burying i.e. its covering through other sedimental layers, a succession of states corresponding to a progressive decrease in the amounts of hydrocarbon compounds and of oxygen-containing compounds which the organic material of the sediments can produce when heated.

Figure 2:
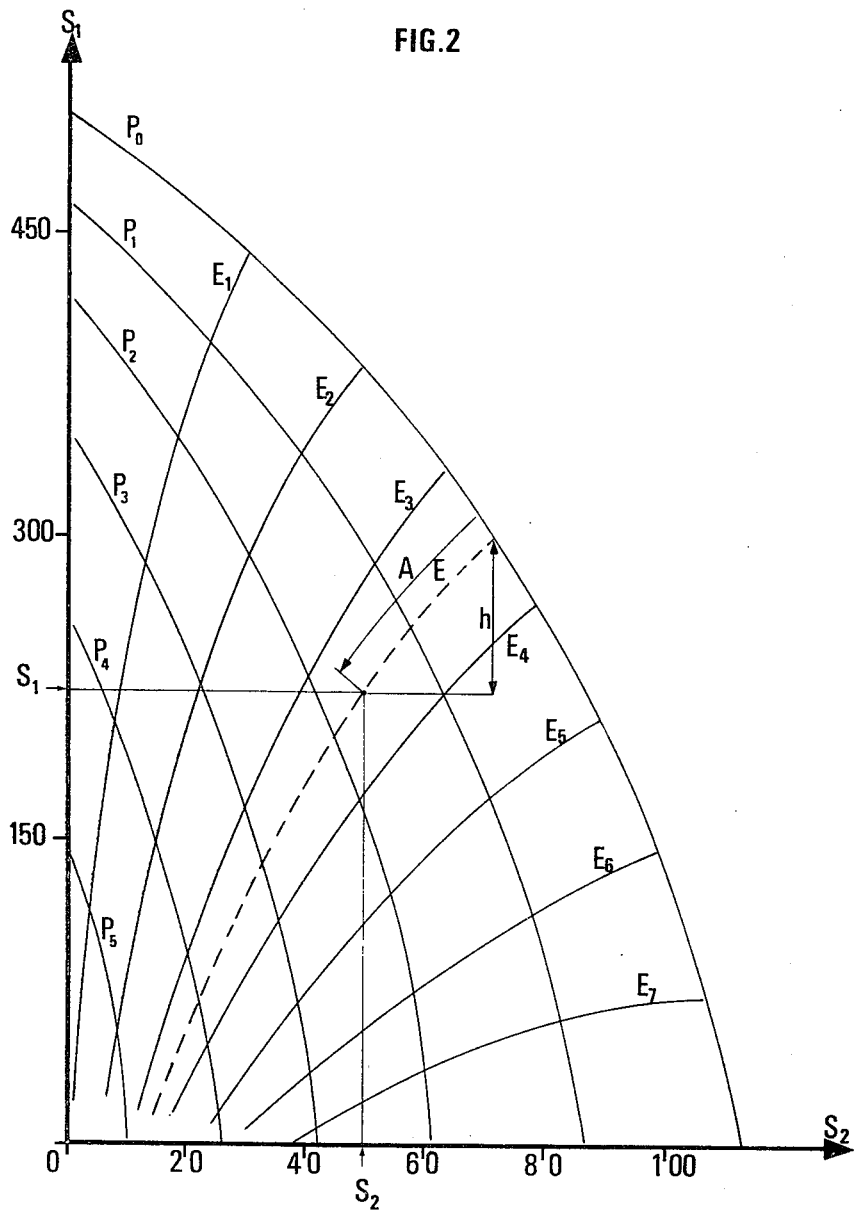
FIG. 2 shows a group of curves obtained for various samples, wherein the productions of the organic material of the sediments respectively on oxygen and hydrocarbon compounds are plotted as abscissae and ordinates.

FIG. 2 shows several curves of evolution $E_1, E_2 \ldots E_7$ for sedimental organic materials having different initial compositions. Thus each curve of evolution characterizes a determined initial composition of the organic material of a sediment.

This figure also shows a certain number of iso-evolution curves, $P_0, P_1 \ldots P_5$, representing distinct sedimentary organic material which have been subjected to the same thermodynamic conditions during the same time interval.

Such a network of curves can be obtained by experimentally determining the pair of values $S_1$, $S_2$ on a certain number of reference samples.

According to the invention, from the couple of values $S_1$, $S_2$ obtained on a sample taken in the ground, or in a drilled well bore, we can determine the ability of the examined sediments to constitute a good mother rock (i.e. source) for hydrocarbons. This ability is the higher as the value $S_1$ is greater and the value $S_2$ lower.

With the chart of FIG. 2, it becomes possible to determine the path of the evolution followed by the organic material of the studied sediment, to estimate the degree of evolution of the organic material contained in this sediment and its capacity to produce hydrocarbon.

The paths of evolution, such as $E_1$ and $E_2$ in the left part of the chart, correspond to the sediments having the highest capacity to produce hydrocarbons (signal $S_1$ corresponding to a high capacity to produce hydrocarbon compounds).

On the other chart we have indicated, by way of example, the point representing a sediment sample characterized by signals $S_1$ and $S_2$. This point representing the sample can be at once located on an interpolated evolution path E (dashed line), and its degree of evolution can be evaluated from the distance A of its actual location on this path from the line $P_o$ corresponding to no evolution, and the remaining capacity of the sediment to produce hydrocarbons can be characterized by the intensity of signal $S_1$.

The distance h characterizes the amount of hydrocarbon products liberated by the sedimentary organic material during its prior evolution.

We will first consider, by way of example, the case of a sample which has been subjected to a preliminary extraction by means of an organic solvent, such as chloroform, in order to eliminate from this sample the hydrocarbons already formed in the sediments.

Figure 3:
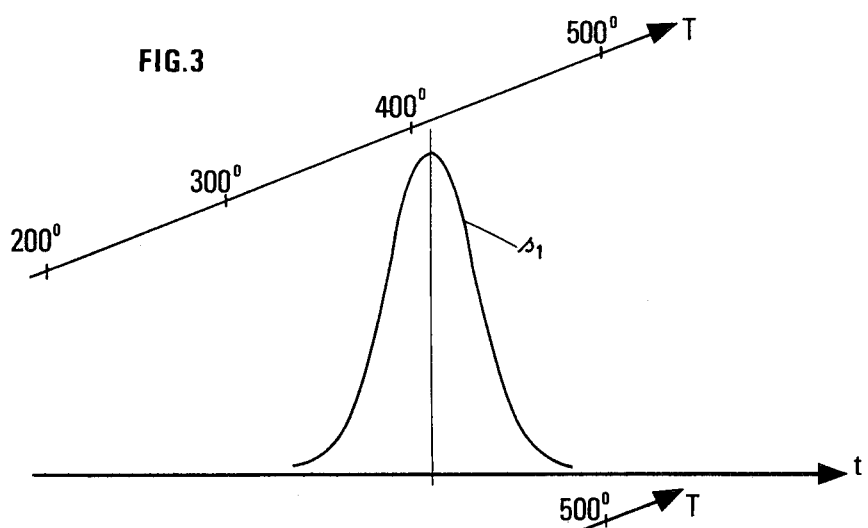
FIG. 3 shows the recording of the content of hydrocarbon compounds in the gas released by heating a sediment sample which has been subjected to a preliminary extraction of the hydrocarbon contained therein, by means of organic solvent.

FIG. 3 shows the recording of signal $S_1$ delivered by the detector 10 of hydrocarbon products other than the hydrocarbons which were already formed in the sediments, as a function of the temperature T of the sample.

The diagram shows a peak having the shape of a Gaussian curve.

This recording may be performed by means (FIG. 1 A) of a recording device 15 of a known type having a first input terminal connected to an output terminal of the detecting device 10 and a second input terminal connected to the thermocouple 5.

The recording device 15 simultaneously records, as a function of time t, the signal $S_1$ whose integral $S_1$ is the desired parameter, and the curve of evolution of the sample temperature T.

Figure 4:
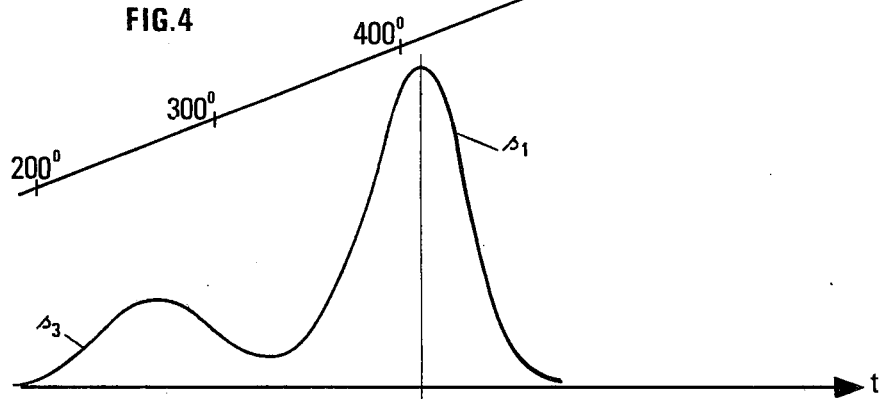
FIG. 4 shows the two successive peaks obtained under the same conditions with a sediment sample which has not been subjected to this solvent extraction.

In the case where the studied rock sample(issued from cores, cuttings . . . etc . . . ) has not been subjected to a preliminary extraction by means of an organic solvent (such as, for example, chloroform), for eliminating the hydrocarbons already formed in the sediments, the device 10 permitting the detection of the amounts of hydrocarbon compounds, delivers a signal $S_3$ corresponding to these already formed hydrocarbons and appearing before the signal $S_1$ (FIG. 4) whose integral $S_1$ is measured.

The signal $S_2$ may represent only a part of the oxygen compounds produced by the organic material contained in the sample, such as for example, the amount of carbon dioxide, or the quantity of water generated by this organic material, the signal $S_1$ still representing the quantity of one or more hydrocarbon compounds produced by the organic material of the sample (i.e. other than the hydrocarbons already present in the sediments).

In such a case, the oxygen-containing compound to be separated will be retained through any suitable means (selective trap which may be of a conventional type, such as a molecular sieve), from the fraction $q_2$ of the gas flow at the outlet of the furnace (FIG. 1).

When the oxygen-containing compound whose content is determined is carbon dioxide, it will be possible, in the case of a sample which has not been preliminarily decarbonated, to progressively raise its temperature from room temperature to a temperature of about 400°C, since the carbon dioxide contained in the carbonates begins to be released at a temperature of about 400°C (it can be noticed that the amount of $CO_2$ released by the mineral matrix of the sediments at 150°C is in fact relatively small as compared to the quantity of $CO_2$ formed by the organic material of these sediments between 150°C and 400°C).

The determination of the production of carbon dioxide through the sediments may be carried out by heating these sediments to a temperature of about 600°C (i.e. within the same temperature range as for the determination of $S_1$), if the sample has been previously subjected to a treatment of decarbonation by an acid (such as, for example, hydrochloric acid), or also in the case of relatively pure organic materials, i.e. which does not substantially contain inorganic materials (such as coals), or organic materials which have been isolated from the mineral matrix of the sediments by chemical destruction of the latter.

In these cases of relatively pure organic material or of decarbonated sediments, it will be possible, after the already formed hydrocarbons have been extracted through an organic solvent, to perform a substantially isothermal measurement of the quantity $S_1$ of one or more hydrocarbon compounds (other than the hydrocarbons already formed in the sediments) and of the quantity $S_2$ of carbon dioxide produced by the organic material of these sediments, by very rapidly heating the sample to a temperature from 450°C to 600°C, advantageously about 550° C.

These hydrocarbon compounds and this carbon dioxide are produced very rapidly upon introduction of the cup 4 into the tube 1 maintained at this substantially constant temperature.

According to another embodiment of the invention, $S_2$ may represent the quantity of water formed by heating the organic material of the sediments.

The measurement will then be performed by heating the sample from about 150°C to about 400°C (below a temperature of about 150°C the measurement would be lead to erroneous results, due to the releasing of water contained in the mineral matrix of the sample and above a temperature of about 400°C, the measurement would also become erroneous due to the formation of water resulting from the dehydroxylation of clayish materials, as already pointed out hereinbefore).

We claim:
1. A process for rapidly evaluating the hydrocarbon production capacity of an organic material from a small sample thereof comprising:
    a. pyrolyzing said sample in a non-oxidizing atmosphere so as to form hydrocarbon compounds and oxygen-containing compounds as products of the pyrolysis of said organic material;
    b. producing a group of two signals $S_1$ and $S_2$, the value of signal $S_1$ being proportional to the quantity of at least one hydrocarbon compound other than the hydrocarbon compounds originally present in said organic material, said at least one hydrocarbon compound being produced by the pyrolysis of said organic material, the value of signal $S_2$ being proportional to the quantity of at least one of the oxygen-containing compounds produced by the pyrolysis of said organic material; and
    c. evaluating from the values of said two signals the capacity of the sediment to constitute a good source for hydrocarbons.

2. The process of claim 1, wherein the temperature of said sample is continuously raised during pyrolysis.

3. The process of claim 2, wherein the temperature of said sample is raised at a rate of about 1°C./minute to 50°C./minute during pyrolysis.

4. The process of claim 1, wherein said organic material is a geological sediment.

5. The process of claim 4, wherein signal $S_1$ is determined by heating said sample to a temperature of about 600°C.

6. The process of claim 4, wherein said sample is heated over a temperature range of at least about from 150° to 450°C during pyrolysis, signal $S_2$ being proportional to the overall amount of said at least one oxygen-containing compound produced by pyrolysis of said organic material over the temperature range of about 150° to 450°C.

7. The process of claim 4, wherein said sample is heated to a temperature of at least about 450°C during pyrolysis, signal $S_2$ being proportional to the amount of carbon dioxide produced by pyrolysis of said organic material as it is heated to about 450°C.

8. The process of claim 4, wherein said sample is substantially free of carbonates, wherein said sample is heated to a temperature of about 600°C, and further wherein signal $S_2$ is proportional to the amount of carbon dioxide produced by pyrolysis of said organic material as it is heated to a temperature of about 600°C.

9. The process of claim 4, wherein said sample is pyrolyzed by heating said sample to a temperature of at least about 450°C, signal $S_2$ being proportional to the amount of water produced during pyrolysis as said sample is heated between about 150° and 450°C.

10. The process of claim 4, wherein said sample is a decarbonated sediment, wherein said decarbonated sediment is subjected to extraction with an organic solvent, wherein pyrolysis of said organic material is accomplished by heating said sample to a temperature in the range of about 450° C to about 600°C, and wherein signals $S_1$ and $S_2$ are proportional respectively to the quantity of said at least one hydrocarbon compound and the quantity of said at least one oxygen-containing compound produced as said sample is pyrolyzed up to said steady temperature.

11. The process of claim 10, wherein said steady temperature is about 550°C.

12. The process of claim 4, wherein said geological sediment is heated to a temperature of at least about 600°C. during pyrolysis, signal $S_2$ being proportional to the amount of said at least one oxygen-containing compound produced as said geological sediment is heated between about 150° and 400°C. during pyrolysis.

13. The process of claim 12, wherein said geological sediment is directly subjected to pyrolysis without being subjected to a preliminary extraction for eliminating hydrocarbons therein, signal $S_1$ being proportional to the amount of said at least one hydrocarbon liberated by said geological sediment between about 325° and 600°C. during pyrolysis.

14. The process of claim 12, wherein said geological sediment is subjected to a preliminary extraction for eliminating the hydrocarbons contained therein, signal $S_1$ being proportional to the total quantity of said at least one hydrocarbon liberated by said geological sediment as said geological sediment is heated up to 600°C. during pyrolysis.

15. A process for rapidly determining the properties of an organic material from a small sample thereof comprising:
 a. pyrolyzing said sample in a non-oxidizing atmosphere to produce a pyrolysis gas product,
 b. producing a first signal proportional to the quantity of at least one hydrocarbon compound other than the hydrocarbon already present in said organic material, produced by the pyrolysis of said organic material, and
 c. producing a second signal proportional to the quantity of at least one oxygen-containing compound produced by pyrolysis of said organic material, said first and second signals indicating the properties of said organic material.

16. The process of claim 15, wherein the temperature of said sample is continuously raised during pyrolysis.

17. A process for rapidly evaluating the hydrocarbon production capacity of a geological sediment from a small sample thereof, said geological sediment containing organic material and ingredients other than organic material, said process comprising:
 a. heating said sample up to a temperature of at least about 600°C in a non-oxidizing atmosphere so as to pyrolyze the organic material in said sample and thereby produce a pyrolysis gas product containing an oxygen-containing gas and hydrocarbons other than hydrocarbons contained in said geological sediment,
 b. measuring the quantity of at least one hydrocarbon other than hydrocarbons originally present in said geological sediment produced during pyrolysis of said organic material as said sample is heated over the temperature range of from about 150°C to at least about 600°C,
 c. measuring the quantity of at least one of said oxygen-containing compounds produced during pyrolysis as said sample is heated over the temperature range of from about 150°C to an elevated temperature above 150°C at which the other materials in said sample liberate said at least one oxygen-containing compound, and
 d. determining the hydrocarbon production capability of said geological sediment by comparing the quantity of said at least one hydrocarbon compound measured in step (b) and the quantity of said at least one oxygen-containing compound measured in step (c).

18. The process of claim 17 wherein said geological sediment contains carbonates, wherein the oxygen-containing gas measured in step (c) is carbon dioxide, wherein only the quantity of carbon dioxide produced during pyrolysis as said sample is heated over the temperature range of about 150°C to at least about 600°C is measured in step (c), and further wherein said sample is decarbonated prior to pyrolysis.

19. The process of claim 17, wherein said geological sediment includes a mineral containing water of hydration, wherein the oxygen-containing gas measured in step (c) is water, and further wherein only the quantity of water produced during pyrolysis as said sample is heated over a temperature range of about 150° to 400°C is measured in step (c).

20. The process of claim 17, wherein the organic material in said geological sediment contains a hydrocarbon soluble in an organic solvent, said process further comprising extracting the hydrocarbon contained in said sample prior to pyrolysis thereof by contacting said sample with said solvent.

21. The process of claim 17, wherein said geological sediment contains carbonates, wherein the oxygen-containing gas measured in step (c) is carbon dioxide, and wherein only the quantity of carbon dioxide produced during pyrolysis as said sample is heated over the temperature range of about 150° to about 450°C is measured in step (c).

22. The process of claim 21, wherein the quantity of carbon dioxide produced during pyrolysis as said sample is heated over the temperature range of about 150° to about 400°C is measured in step (c).

23. The process of claim 17, wherein said geological sediment contains an originally present hydrocarbon present in said geological sediment prior to pyrolysis, said originally present hydrocarbon substantially completely volatilizing at a temperature lower than the temperature at which pyrolysis of the remaining portion of the organic material in said geological sediment begins, the quantity of originally present hydrocarbon obtained during pyrolysis being excluded from the quantity of said at least one hydrocarbon measured in step (b).

24. The process of claim 23, wherein said geological sediment contains a hydrocarbon component which substantially completely volatilizes at a temperature of about 325°C, only that portion of said at least one hydrocarbon compound obtained during pyrolysis as said sample is heated to a temperature above about 325°C being measured in step (b).

25. A process for rapidly evaluating the hydrocarbon production capacity of a geological sediment containing mineral and organic components, said organic component including volatilizable hydrocarbons and a remaining portion, said process comprising:
 a. pyrolyzing a small sample of said geological sediment by heating to a temperature sufficiently high so that (1) the volatilizable hydrocarbons in said geological sediment are volatilized and (2) thereafter the remaining portion of said organic component is pyrolyzed to form hydrocarbon pyrolysis products, pyrolysis of said sample further producing oxygen-containing pyrolysis product compounds,
 b. measuring the quantity of at least one of said hydrocarbon pyrolysis products,
 c. measuring the quantity of at least one of said oxygencontaining pyrolysis product compounds, and
 d. comparing the quantity of said at least one hydrocarbon pyrolysis product and the quantity of said at least one oxygencontaining pyrolysis product compound to determine the capacity of said sediment to produce hydrocarbons.

26. A process for rapidly evaluating the hydrocarbon production capacity of a geological sediment containing mineral and organic components, said organic component including volatilizable hydrocarbons and a remaining portion, said process comprising:
 a. heating in a non-oxidizing atmosphere a small sample of said geological sediment from below about 150°C to an elevated temperature at which pyrolysis of the organic material in said geological sediment is substantially complete, said heating effecting volatilization of the volatilizable hydrocarbons in said sample and pyrolysis of the remaining portions of the organic component of said sample, said heating continuously producing a pyrolysis gas product containing hydrocarbons and oxygen-containing compounds, b. continuously feeding at least a portion of the pyrolysis gas product produced in step (a) to a first measuring means for measuring the concentration of at least one hydrocarbon contained in said pyrolysis gas product, c. integrating the concentration of said at least one hydrocarbon in the pyrolysis gas product fed to said first measuring means over a predetermined time period to obtain the total amount of said at least one hydrocarbon produced in step (a) over said time period, said time period commencing after volatilization of the volatilizable hydrocarbons in said sample is substantially complete and ending after pyrolysis of the remaining portion of the organic component in said sample is substantially complete, d. continuously feeding at least a portion of said pyrolysis gas product to a second measuring means for measuring the quantity of said at least one oxygen-containing component in the pyrolysis gas product fed thereto, and e. measuring in said second measuring means the total amount of said oxygen-containing compound produced in step (a) from the time when the temperature of said sample in step (a) is 150°C to the time when the temperature of said sample in step (a) is high enough to cause the mineral component in said sample to liberate quantities of the oxygen-containing compound being measured in step (d).

27. The process of claim 26, wherein the mineral component of said geological sediment contains carbonates, wherein the oxygen-containing compound being measured in step (d) is carbon dioxide, and further wherein the only carbon dioxide measured in step (d) is the carbon dioxide produced in step (a) as the temperature of the sample varies from about 150° to about 450°C.

28. Apparatus for rapidly evaluating the hydrocarbon production capacity of an organic material from a small sample thereof comprising:

a. means for heating said sample in a non-oxidizing atmosphere so as to pyrolyze said organic material and form a pyrolysis gas product;

b. means for producing a signal $S_1$ proportional to the quantity of at least one hydrocarbon compound produced by pyrolysis of said organic material when heating said sample; and c. means for producing a signal $S_2$ proportional to the quantity of at least one oxygen-containing compound produced by pyrolysis of said organic material when heating said sample, signals $S_1$ and $S_2$ permitting an evaluation of the capacity of said sediment to constitute a good source for hydrocarbons.

29. The apparatus of claim 28, further comprising means for separating said pyrolysis gas product into a first gas stream and a second gas stream, said means for producing a signal $S_1$ being constructed so as to measure the quantity of said at least one hydrocarbon compound in said first gas stream, said means for producing signal $S_2$ being constructed so as to measure the quantity of said at least one oxygen-containing compound in said second gas stream.

30. The apparatus of claim 29, wherein said heating means comprises a furnace provided with a support member for said sample and inlet means for supplying a pressurized gas for conveying said pyrolysis gas product out of said furnace.

31. The apparatus of claim 29, wherein said means for producing a signal $S_1$ includes measuring means for continuously measuring the instantaneous concentration $s_1$ of said at least one hydrocarbon compound in said first gas stream and integrating means for integrating the instantaneous concentration $s_1$ with respect to time to produce signal $S_1$.

* * * * *